United States Patent [19]

Dhabhar et al.

[11] 4,130,638

[45] Dec. 19, 1978

[54] MOUTHWASH COMPOSITIONS

[75] Inventors: Dadi J. Dhabhar; Allen Heyd, both of Norwalk, Conn.; Eugene H. Gans, Hastings-on-Hudson, N.Y.

[73] Assignee: Richardson-Merrell Inc., Wilton, Conn.

[21] Appl. No.: 853,221

[22] Filed: Nov. 21, 1977

Related U.S. Application Data

[63] Continuation-in-part of Ser. No. 738,584, Nov. 3, 1976, abandoned.

[51] Int. Cl.$^2$ .......................... A61K 7/16; A61K 7/24
[52] U.S. Cl. ........................ 424/55; 424/49; 424/58
[58] Field of Search ...................... 424/49–58

[56] References Cited

U.S. PATENT DOCUMENTS

| | | | |
|---|---|---|---|
| 1,633,336 | 6/1927 | Larson | 424/55 |
| 1,936,456 | 11/1933 | Larson | 424/55 |

OTHER PUBLICATIONS

Demers et al., J. Periodont. 38:294–301, Jul.–Aug. 1967.
Jones, Brit. J. Dent. Sci. 70:171–179, (1927).
Hartzell, J. Am. Dent. Assoc., vol. XII:1452–1467, Dec. 1925.
Windholz et al., Merck Index 9th Ed., (1976), p. 1077, Entry "Saccharin," p. 1077, Entry "Saccharin Soluble," Merck & Co., Rathway, N. J.

*Primary Examiner*—Shep K. Rose
*Attorney, Agent, or Firm*—George W. Rauchfuss, Jr.; Eugene O. Retter

[57] ABSTRACT

Physiologically acceptable mouthwash formulations containing sodium ricinoleate substantially free of haze and precipitation.

7 Claims, No Drawings

MOUTHWASH COMPOSITIONS

RELATED APPLICATIONS

This application is a continuation-in-part of application Ser. No. 738,584, filed Nov. 3, 1976, now abandoned.

FIELD OF THE INVENTION

This invention relates to improved oral compositions of sodium ricinoleate which are substantially free of haze and precipitation and yet are physiologically acceptable and effective as anti-plaque and calculus compositions and useful in the treatment of periodontal disease.

BACKGROUND OF THE INVENTION

The use of sodium ricinoleate, the sodium salt of mixed fatty acids from castor oil, in the treatment of periodontal disease and as an effective anti-plaque and anti-calculus agent has long been recognized, such as, for example, as disclosed in Demers, D. G. et al., Journal of Periodontology, Vol. 38, pp 294–301, July-August 1967; Jones, H. E., British Journal of Dental Science, Vol. 70, pp 171–179, 1927 and Hartzell, T. B., Journal American Dental Association, XII, pp 1452–67, December 1925. In addition, in U.S. Pat. No. 1,633,336 a castor oil soap is disclosed as being useful in a dentifrice to render mouth bacteria harmless. The use of sodium ricinoleate in an oral preparation for use as a mouthwash or dental product is disclosed in U.S. Pat. No. 1,936,456 issued to the Wm. S. Merrell Company. Moreover, the Wm. S. Merrell Company marketed such as oral preparation in a toothpaste, powder and mouthwash form under the trademark DETOXOL. The active ingredient of said products was sodium ricinoleate, namely, sodium 12-hydroxy-9-octadecenoate, known as Soricin, the major component of castor oil soap.

The marketing of such products has, however, not been entirely successful due at least in part to the instability and insolubility of sodium ricinoleate in the compositions which results in undesirable haze formation and precipitation. The solubility of sodium ricinoleate and its related fatty acid salts is limited by the pH of the aqueous system they are dissolved in. In water the solubility of sodium ricinoleate decreases with decrease in concentration because the pH is a direct function of fatty acid concentration. The un-ionized species at pH 8 or below in water, are essentially insoluble and therefore show instability. An aqueous solution of sodium ricinoleate at pH 7.9 forms a heavy haze precipitate and is milky white and completely opaque white at pH 7.0 and below.

Soluble salts of ricinoleate and its related salts can be used but they require a very high pH, pH 9–10, and/or solvent concentration to keep the hydrolyzed form in solution. However, both high pH and solvent concentration are unsuitable or undesirable for physiological application. Furthermore, sodium ricinoleate and the related materials are adversely affected by many things which are normally part of a pharmaceutical formulation such as heavy metal ions, cations, ionic salt effect, oxygen and oxidizing agents.

Moreover, in determining the effectiveness of a substance as a plaque inhibitor the contact angle becomes an important determining factor. The contact angle is a measure of the hydrophobicity of a treated surface determined by measuring the angle a sessile drop of water makes with the treated surface. The greater the angle the more hydrophobic the surface is. Sodium ricinoleate has a limited long term solubility in water at concentrations pharmaceutically acceptable at its upper range and clinically effective at the lower range. As a result, within the concentration range where sodium ricinoleate is effective, as demonstrated by contact angle on tooth or hydroxyapatite surface, a physically unacceptable haze or floc is formed in aqueous solution. Other solvents or additives can increase the solubility of sodium ricinoleate but such solutions tend to produce only minimal adsorbed layers of sodium ricinoleate on the tooth surface with low contact angles of reduced durability. For example, in solutions of sodium ricinoleate in alcohol, the contact angle decreases from 135° in water to less than 50° in alcohol. Likewise, although surfactants can increase the solubility of sodium ricinoleate in water, there is, however, a resultant severe reduction in the contact angle of the composition.

There is, therefore, a need for formulation of a special sodium ricinoleate composition that provides a concentration of sodium ricinoleate above the acceptable level in pure water without decrease in its anti-plaque and calculus activity, as exhibited by substantially no loss of or reduced durability of its contact angle or absorbed layer on the tooth surface and with sodium ricinoleate solubility and liquid clarity acceptable for a mouthwash type product.

DESCRIPTION OF THE INVENTION

The invention comprises sodium ricinoleate mouthwash compositions substantially free of haze and precipitation and wherein each of the components of these compositions is present in such a concentration that they collectively cause sodium ricinoleate to be solubilized and stabilized, without loss of contact angle or contact angle durability, and in which each of the components singularly has its own optimum effect on solubility and stability but of a kind much less than the collective combination. Such compositions are those of the following approximate formulation:

| | |
|---|---|
| 10 to 25% v/v | alcohol |
| 5 to 15% v/v | sorbitol |
| 0.5 to 2.5% w/v | surfactant |
| 0.25 to 1% w/v | sodium chloride |
| 0.05 to 0.2% w/v | insoluble saccharin |
| 0.01 to .25% w/v | flavoring |
| 0.1 to 2% w/v | sodium ricinoleate |
| q.s. | water | wherein the flavoring agent is selected from menthol, thymol, eucalyptol, and anethol and mixtures thereof with peppermint oil. A preferred range of sodium ricinoleate is 0.25 to 1% w/v.

Additionally, although not essential it is contemplated that other ingredients normally found in mouthwash compositions may be added to the compositions of this invention, such as, for example, antioxidants or stabilization agents, metal complexing agents, dyes or coloring agents and the like. These ingredients may be incorporated in the instant compositions in amounts which do not adversely affect the properties and characteristics of the compositions of this invention.

DETAILED DESCRIPTION OF THE INVENTION

The optimum pH range for the sodium ricinoleate mouthwash compositions of this invention is between 7.3 and 7.8. However, to obtain a sodium ricinoleate mouthwash composition in said pH range without the formation of haze and a precipitate yet maintaining high contact angles of long duration has not heretofore been considered possible. It is only with the combination of components in the ranges specified hereinbefore that it has been possible to obtain such clear, stabilized sodium ricinoleate mouthwash compositions effective in inhibiting plaque and calculus. Compositions formulated according to this invention in the pH range of 7.3 to 7.8 remain stable and clear for six months at room temperature and at 37° C., and three months at 45° C. whereas prior art compositions were incapable of remaining clear and stable at such temperatures.

As stated previously, the combination of components forming the sodium ricinoleate mouthwash compositions of this invention and present in the prescribed ranges causes the sodium ricinoleate to be solubilized and stabilized and this without loss of contact angle or contact angle duration and the results of the combination are greater and different in kind than the combined effect of each component singularly. For example, whereas an aqueous composition of 0.5% w/v sodium ricinoleate has a contact angle of 135°, when alcohol is added in an amount of 10, 15 and 25% v/v, the contact angle drops to approximately 124°, 120° and 108°, respectively, and when all the water is replaced by alcohol the contact angle drops to approximately 50°. Yet, a composition of this invention containing 10 to 25% v/v alcohol has a contact angle of approximately 130° and also has improved clarity and stability. Likewise, surfactants, such as a Pluronic F-127, when added to aqueous solutions of sodium ricinoleate decrease the contact angle by about 10° to 15° yet no such decrease is evident in a composition of this invention.

Although insoluble saccharin and sodium saccharin are known in the art for mouthwash formulations, it has been discovered that only insoluble saccharin leads to a sodium ricinoleate mouthwash composition with the desirable improved properties of this invention. Likewise, although numerous flavoring agents have been used in mouthwash formulations heretofore, only menthol, thymol, eucalyptol and anethol or mixtures thereof with peppermint oil have been found to give the solubilization and stabilization results desired for a composition of this invention.

Organic surface-active agents used in the compositions of the present invention assist in achieving thorough and complete dispersion of the instant compositions throughout the oral cavity, and render the instant compositions more cosmetically acceptable. The organic surface active material may be anionic, nonionic ampholytic or cationic in nature. Suitably such detergents and water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1.2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last-mentioned amides are N-lauroyl sarcosine, and the sodium, potassium and ethanolamine salts of N-lauroyl, N-myristoyl, or N-palmitoyl sarcosinates, which should be substantially free from soap or similar higher fatty acid material which tends to substantially reduce the effect of these compounds.

Other suitable surface active materials include nonionic agents, such as, fatty acid partial esters of sorbitol anhydride (Span surfactants), polyoxyethylene sorbitol fatty acid esters (Tween surfactants), such as condensates of sorbitan monostearate with approximately 60 moles of ethylene oxide, condensates of ethylene oxide with propylene oxide condensates of propylene glycol (Pluronics surfactants) and cationic surface active germicides and antibacterial compounds such as di-isobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly)oxyethylene groups attached to the nitrogen (typically containing a total of from about 2 to 50 ethenoxy groups per molecule) and salts thereof with acids, and compounds of the structure

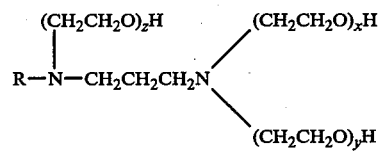

where R is a fatty alkyl group containing from about 12 to 18 carbon atoms, and x, y, and z total 3 or higher, as well as salts thereof with mineral or organic acids.

As indicated hereinbefore other ingredients normally found in mouthwash compositions may be incorporated in amounts not adversely affecting the properties and characteristics of the compositions of this invention. For example, antioxidants, of which butylated hydroxytoluene and butylated hydroxyanisole are exemplary, may be incorporated in amounts of from about 0.001 to 0.1% w/v. Metal complexing agents, of which tetrasodium ethylenediaminetetraacetic acid may be mentioned as exemplary, may be incorporated in amounts of from about 0.001 to 0.1% w/v. Dyes or coloring agents, such as, for example, FD & C Blue #1 dye, can be incorporated in amounts of from about 0.0001 to 0.001% w/v.

As an illustrative example of an especially preferred sodium ricinoleate mouthwash composition of this invention there may be mentioned the following composition:

| | |
|---|---|
| alcohol | 10% v/v |
| sorbitol | 10% v/v |
| Pluronic F-127 surfactant | 0.75% w/v |
| sodium chloride | 0.5845% w/v |
| insoluble saccharin | 0.10% w/v |
| menthol | 0.13% w/v |
| peppermint oil | 0.09% w/v |
| tetrasodium ethylenediamine- | |

| | |
|---|---|
| tetraacetic acid | 0.0114% w/v |
| butylated hydroxyanisole | 0.0005% w/v |
| citric acid, hydrous | 0.0525% w/v |
| FD & C Blue #1 | 0.0003% w/v |
| sodium ricinoleate | 0.25 to 2% w/v |
| distilled water | q.s. |

Such a mouthwash is formed by measuring out the appropriate volume of water into a suitable container equipped with a stirrer and dissolving therein the following ingredients in the given order: sodium chloride, sodium ricinoleate, insoluble saccharin, sorbitol, citic acid and tetrasodium ethylenediaminetetraacetic acid.

In another suitable sized container there is measured out the alcohol and in this is dissolved, with stirring, the Pluronic surfactant, menthol, peppermint oil and butylated hydroxyanisole. Thereafter this solution is transferred to the container holding the first solution and mixed. The dye is added to a small volume of purified water and added to the mouthwash solution and the mouthwash composition is then brought up to its final volume with purified water and mixed for approximately 15 minutes.

Pluronic F-127 is an α-hydro-omega-hydroxypoly(oxyethylene)poly(oxypropylene) (55-61 moles) polyoxyethylene block copolymer having a molecular weight ranging from about 9700 to 13,200, an average molecular weight of about 11,500, a melting point of 56° C. and a cloud point above 100° C. in 1 percent aqueous solution and approved as food additives — Federal Register, Vol. 35, No. 185, pp 14769-70, Sept. 23, 1970.

It will be apparent that various modifications may be made in the examples which fall within the scope of the invention without departing from the spirit and scope of the invention.

We claim:

1. A sodium ricinoleate mouthwash composition substantially free of haze and precipitation comprising about:

| | |
|---|---|
| 10 to 25% v/v | alcohol |
| 5 to 15% v/v | sorbitol |
| 0.5 to 2.5% w/v | surfactant |
| 0.25 to 1% w/v | sodium chloride |
| 0.05 to 0.2% w/v | insoluble saccharin |
| 0.01 to .25% w/v | flavoring |
| 0.1 to 2% w/v | sodium ricinoleate |
| q.s. | water | and wherein the flavoring agent is selected from the group consisting of menthol, thymol, eucalyptol and anethol or mixtures thereof with peppermint oil.

2. A composition of claim 1 wherein the composition also contains about 0.001 to 0.1% w/v of an antioxidant for the sodium ricinoleate.

3. A composition of claim 2 wherein the antioxidant is selected from butylated hydroxytoluene and butylated hydroxyanisole.

4. A composition of claim 3 wherein the composition also contains about 0.001 to 0.1% w/v of a metal complexing agent.

5. A composition of claim 4 wherein the metal complexing agent is tetrasodium ethylenediaminetetraacetic acid.

6. A composition of claim 5 comprising about

| | |
|---|---|
| 10% v/v | alcohol |
| 10% v/v | sorbitol |
| 0.75% w/v | surfactant |
| 0.5845% w/v | sodium chloride |
| 0.10% w/v | insoluble saccharin |
| 0.13% w/v | menthol |
| 0.09% w/v | peppermint oil |
| 0.0114% w/v | tetrasodium ethylenediaminetetraacetic acid |
| 0.0005% w/v | butylated hydroxyanisole |
| 0.0525% w/v | citric acid |
| 0.0001 to 0.001% w/v | dye |
| 0.25 to 1.0% w/v | sodium ricinoleate |
| q.s. | water |

7. The composition of claim 6 wherein the sodium ricinoleate is present in an amount of 1% w/v.

* * * * *